(12) United States Patent
Zhu et al.

(10) Patent No.: US 11,634,656 B2
(45) Date of Patent: Apr. 25, 2023

(54) HYDROPHILIC LUBRICATING COATING FOR MEDICAL CATHETERS AND ITS PREPARATION METHOD

(71) Applicant: OrbusNeich Medical PTE. LTD., Singapore (SG)

(72) Inventors: Jingjing Zhu, Guangdong (CN); Songyun Xu, Guangdong (CN); Mian Li, Guangdong (CN); Chang Peng, Guangdong (CN); Yirong Gong, Guangdong (CN)

(73) Assignee: OrbusNeich Medical PTE. LTD., Singapore (SG)

(*) Notice: Subject to any disclaimer, the term of this patent is extended or adjusted under 35 U.S.C. 154(b) by 141 days.

(21) Appl. No.: 16/919,477

(22) Filed: Jul. 2, 2020

(65) Prior Publication Data

US 2020/0339906 A1    Oct. 29, 2020

(51) Int. Cl.
*C10M 169/04* (2006.01)
*A61L 29/08* (2006.01)
(Continued)

(52) U.S. Cl.
CPC ....... *C10M 169/041* (2013.01); *A61L 29/085* (2013.01); *A61L 29/14* (2013.01);
(Continued)

(58) Field of Classification Search
CPC .... A61L 29/085; A61L 29/14; A61L 2420/02; A61L 2420/06; A61L 2400/10;
(Continued)

(56) References Cited

FOREIGN PATENT DOCUMENTS

| CN | 101812265 A | 8/2010 | |
| CN | 107376029 A | * 11/2017 | ........... A61L 29/085 |

(Continued)

*Primary Examiner* — Vishal V Vasisth
(74) *Attorney, Agent, or Firm* — Leason Ellis LLP

(57) ABSTRACT

The invention discloses a photocured medical catheter hydrophilic lubricating coating and a preparation method thereof. The hydrophilic lubricating coating comprises a primer coating and a lubricating coating. The primer coating is attached to the surface of a device, and the lubricating coating is attached to the primer coating. The primer coating comprises 1-10 parts by weight of one or more polyester acrylates, 50-90 parts by weight of one or more solvents, 0.5-5 parts by weight of one or more photoinitiators, 0.5-2 parts by weight of one or more wetting agents and 0.5-5 parts by weight of one or more reactive (or active) diluents. The lubricating coating comprises 1-10 parts by weight of one or more water soluble macromolecules, 1-5 parts by weight of one or more crosslinking (or crosslinked) macromolecules, 0-1 part by weight of one or more photoinitiators, 0.1-1 part by weight of one or more surfactants and 50-98 parts by weight of one or more solvents. The preparation method of the hydrophilic lubricating coating is simple and easy in operation. Substance residues caused by complicated high-temperature chemical reactions are avoided. The cured coating forms a crosslinking (or crosslinked) structure, has good adhesion on the surface of a medical catheter and has excellent and lasting lubricity in an aqueous medium. The friction coefficient of the surface of the medical catheter is reduced. Harm to human tissues and adhesion of macromolecules in blood are decreased.

17 Claims, 1 Drawing Sheet

(51) Int. Cl.
*A61L 29/14* (2006.01)
*B05D 3/06* (2006.01)
*B05D 3/10* (2006.01)
*C10M 107/32* (2006.01)
*C10M 107/34* (2006.01)
*C10M 107/42* (2006.01)
*C10M 155/02* (2006.01)
*C10N 40/00* (2006.01)
*C10N 50/00* (2006.01)

(52) U.S. Cl.
CPC ............... *B05D 3/067* (2013.01); *B05D 3/10* (2013.01); *C10M 107/32* (2013.01); *C10M 107/34* (2013.01); *C10M 107/42* (2013.01); *C10M 155/02* (2013.01); *A61L 2400/10* (2013.01); *A61L 2420/02* (2013.01); *A61L 2420/06* (2013.01); *A61L 2420/08* (2013.01); *C10M 2209/1023* (2013.01); *C10M 2209/1045* (2013.01); *C10M 2217/0285* (2013.01); *C10M 2229/02* (2013.01); *C10N 2040/50* (2020.05); *C10N 2050/023* (2020.05)

(58) Field of Classification Search
CPC ....... A61L 2420/08; B05D 3/067; B05D 3/10; B05D 7/542; B05D 5/08; B05D 2254/02; B05D 2201/00; C10M 107/34; C10M 107/32; C10M 107/42; C10M 155/02; C10M 169/041; C10M 2217/0285; C10M 2209/1045; C10M 2229/02; C10M 2209/1023; C10N 2040/50; C10N 2050/023; C08L 39/06
See application file for complete search history.

(56) References Cited

FOREIGN PATENT DOCUMENTS

| | | |
|---|---|---|
| CN | 107376029 A | 11/2017 |
| CN | 107412883 A | 12/2017 |
| CN | 109045367 A | 12/2018 |

* cited by examiner

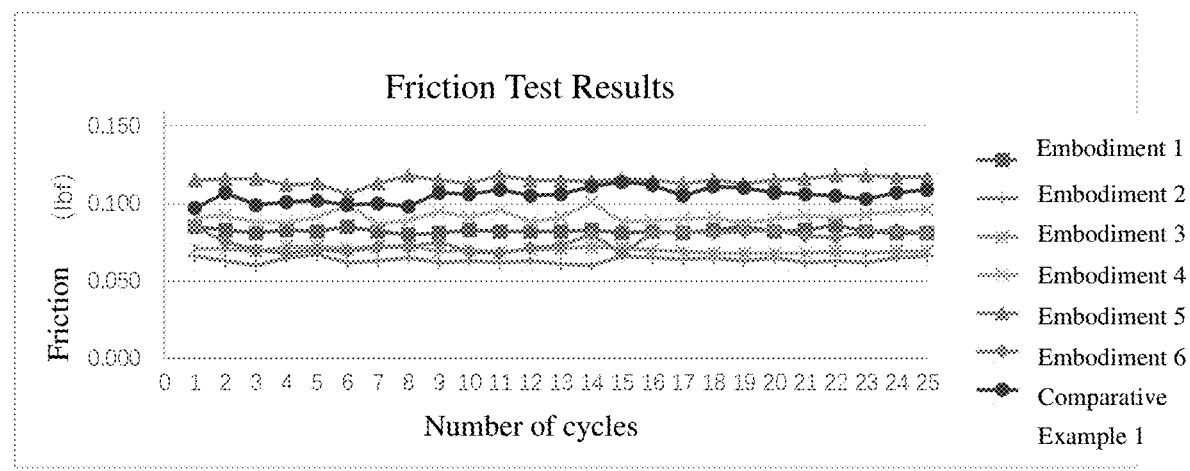

HYDROPHILIC LUBRICATING COATING FOR MEDICAL CATHETERS AND ITS PREPARATION METHOD

TECHNICAL FIELD

The invention relates to the technical field of medical devices, in particular to a photocured hydrophilic lubricating coating for medical catheters and a preparation method thereof.

BACKGROUND TECHNOLOGY

Interventional catheters are widely used in clinical treatment. Many devices intended for short-term or long-term contact with human tissues, such as balloon catheters, guiding catheters and guidewires, will rub against the contacted tissues during insertion or withdrawal. Consequently, it is difficult for the device to reach the designated lesion, which is unfavorable for clinical practice, and may cause adverse reactions such as tissue damage and inflammation. In order to reduce the risk of surgery and suffering of patients, various lubricating coatings have been developed for medical catheters. In recent years, people have turned their research focus to hydrophilic lubricating coatings with water solubility and biocompatibility. Hydrophobic lubricants such as silicone oil, olive oil, petroleum jelly, etc. have many disadvantages including poor lubricity, poor adhesion, poor durability, and inconvenience of surgery. Hydrophilic lubricating coating overcomes such disadvantages and greatly reduces the friction coefficient of the catheter surface, thus minimizing damage to human body and bringing great convenience for interventional procedures.

Many methods of using hydrophilic coatings to improve the lubricity of medical devices are well known. In an aqueous environment such as human blood, it is difficult for the hydrophilic coating remain on the surface of the medical catheter with long-lasting lubrication.

A type of polymers such as polyethylene oxide, polyvinylpyrrolidone, etc., can transfer into a hydrogel by absorbing water in an aqueous environment, thereby showing good lubricity. Such hydrophilic substances are selectively connected or polymerized on the surface of the substrate through polyester or polyurethane, (meth) acrylate polymer or copolymer, (meth) acrylic polymer or copolymer, maleic anhydride, etc.

However, in the process of use, the coating is easily peeling off from the surface or damaged due to the weak bond between the coating and the surface of the material, resulting in unstable and nondurable of hydrophilic lubrication. The firmness and durability of the surface can be increased by using polymers with crosslinkable reticular structures or polymers with semi-interpenetrating network structure.

These cross-linked materials are usually cured by heat or light. The method of heat curing takes a long time and the production efficiency is lower. UV light is usually used for light curing. After the substances receive or absorb external energy, they change chemically and decomposes into radicals or cations, thereby initiating polymerization. The radical polymerization is more sensitive to oxygen inhibiting, and inert gas is needed to protect the polymerization process. While the cationic polymerization is more sensitive to alkaline and humid conditions, requiring strict polymerization conditions.

Currently, the coating is made with certain lubricity and hydrophilicity to achieve the lubricating function, but existing technologies of the lubricating coating has some disadvantages including complex coating preparation process, high cost, long heating and curing time, low production efficiency, poor adhesion, unsatisfactory lubricity and durability.

Patent CN 104558658 A discloses a method for preparing a coating on intervention catheter surface: add water-based polyurethane, multifunctional aziridine derivatives, polyether modified polysiloxane and deionized water into the container and stir for 20 to 50 minutes at room temperature to obtain the primer coating solution; add polymethylvinyl ether-maleic anhydride, acrylic acid, hydroxyethyl acrylate, multifunctional acrylate derivatives, photoinitiator and organic solvent into a container and stir for 20 minutes to 50 minutes at room temperature to obtain the top coating solution. Coating preparation: apply the primer solution to the surface of intervention catheter grafted with acrylic to obtain the primer coating after curing; then apply the top coating solution onto the primer coating to obtain the top coating after curing. Post-treatment: the intervention catheter coated with the primer coating and the top coating is exposed to ultraviolet light for 5 min~15 min, then immersed into concentrated ammonia water, soaked for 1 h~2 h at room temperature, taken out and dried. The hydrophilic lubricating coating prepared by this method has good lubricity and firmness, but the preparation process is complicated, and the grafting time and thermal curing time are too long, which greatly reduces the production efficiency.

Another example is the patent CN 106540336 A, which discloses a hydrophilic modified coating on the surface of medical intervention catheters, which is composed of a transition coating and a lubricating coating. The composition of the transition coating and the weight parts of each component are: adhesive resin 5-10 parts, photoinitiator I 0.1-0.2 parts, leveling agent 0.05-0.1 part, solvent I 85-95 parts. The composition of the lubricating coating and the weight parts of each component are: hydrophilic resin 5-10 parts, water-based crosslinking agent 1-5 parts, photoinitiator II 0.2-0.5 parts, solvent II 80-95 parts. However, the coating preparation process takes a long time, and the viscosity of the lubricating coating is high, which is easy to result in thick and uneven surface coating, and requires high-quality coating techniques.

Therefore, a hydrophilic lubricating coating for medical catheters with rapid curing ability and firm and durable lubricity to improve the comfort of patients using catheters, has become an urgent problem to study and solve in this field.

SUMMARY OF THE INVENTION

The technical problem to be solved by this invention is to provide a photocurable medical catheter hydrophilic lubricating coating and its preparation method in current technical situation, which solves problems including the adhesion, lubricity, durability, rapid curing, etc. The rapidly curing hydrophilic coating gives medical catheters good hydrophilic properties, good adhesion, and long-lasting lubricity.

To achieve the above objectives, this invention adopts the following technical solutions:

One aspect of the present invention is to provide a photocurable hydrophilic lubricating coating for medical catheter, comprising a primer coating applied to the device surface and the lubricating coating on the top of the primer coating, in which:

The said primer coating includes the following parts by weight of components: polyester acrylate 1-10 parts, solvent 50-90 parts, photoinitiator 0.5-5 parts, wetting agent 0.5-2 parts and reactive diluent 0.5-5 parts.

The said lubricating top coating includes the following parts by weight of components: water-soluble macromolecules 1-10 parts, cross-linked macromolecules 1-5 parts, photoinitiator 0-1 part, surfactant 0.1-1 part and mixed solvent 50-98 parts.

Further, said polyester acrylate is a water-soluble resin.

Further, said polyester acrylate is an aliphatic resin.

Further, said polyester acrylate has an unsaturated functionality with one or more oligomers selected from 3 functional polyester acrylate, 4 functional polyester acrylate and 6-functionality polyester acrylate.

Further, said solvent is selected from ethanol, propanol or isopropanol.

Further, said coating is one or more selected from 2-hydroxy-4'-(2-hydroxyethoxy)-2-methylpropiophenone (IRGACURE 2959), 2-hydroxy-2-methylpropiophenone (DAROCUR 1173), benzophenone and methyl benzoylformate.

Further, said wetting agent is selected from polyether modified organosilicone or polyether modified organosiloxane.

Further, said reactive diluent is one or more of single-functional active diluent and multi-functional active diluent.

Further, said reactive diluent is one or more of vinylpyrrolidone, hydroxyethyl methacrylate, ethoxyethoxyethyl acrylate and propylene oxide neopentyl glycol diacrylate.

Further, said water-soluble macromolecules are selected from one or more of polyvinylpyrrolidone, polyethylene glycol, polyethylene oxide, and polyvinyl alcohol.

Further, said cross-linked macromolecules are water-soluble.

Further selectively, said cross-linked macromolecules are oxygen-insensitive cross-linked substances, and has a light-absorbing functional group or a chromophore, and can self-luminously polymerize under UV light without adding a photoinitiator.

Further selectively, said cross-linked macromolecule are oxygen-sensitive substances, which can be polymerized under UV light by adding a small amount of photoinitiator.

Further, said cross-linked macromolecules are capable of cross-linking to form a network structure, which is both water-insoluble and water-swellable.

Further selectively, said cross-linked macromolecules are one or more of polyvinyl alcohol pyridines, waterborne polyurethane, trimethylolpropane triacrylate.

Further, said surfactant is a water-soluble nonionic surfactant, and is selected from one or more of polyethylene glycol and polyethylene oxide.

Further, said mixed solvent is a mixture of alcohol and water, wherein the alcohol solvent is selected from ethanol, propanol or isopropanol.

The second aspect of the present invention is to provide a preparation method of said photocurable hydrophilic lubricating coating for medical catheters, comprising following steps:

S1: Preparation of the primer coating:
S11: Weigh each component by said parts of weight of the primer coating;
S12: Add solvent, reactive diluent, photoinitiator and wetting agent into the polyester acrylate in sequence, and stir for 1-3 h in the dark to obtain the primer coating, which should be stored away from light;

S2: Preparation of the lubricating coating:
S21: Weigh each component by said parts of weight of the lubricating coating;
S22: Add mixed solvent, cross-linked macromolecules, surfacant and photoinitiator into the water-soluble macromolecules in sequence, and stir for 1-3 h in the dark to obtain the lubricating coating, which should be stored away from light;

The third aspect of the present invention is to provide a method for using said photocurable hydrophilic lubricating coating for medical catheters, comprising following steps:

S31: Wipe the medical catheter to be treated with a clean cloth dipped in absolute ethanol to remove dirt on the surface and dry;

S32: Uniformly apply said primer coating in claim 18 on the cleaned medical catheter by dipping, spraying or brushing, and cure the surface of the catheter under ultraviolet light to form a primer coating.

S33: Uniformly apply said lubricating coating in claim 18 on the primer coating of medical catheter by dipping, spraying or brushing, and cure the surface of the catheter under ultraviolet light to form a hydrophilic lubricating coating.

In summary, in the photocurable hydrophilic lubricating coating for medical catheters provided by the present invention, the primer coating adopts polyester acrylic resin, which has good coating adhesion and fast ultraviolet curing speed. The lubricating coating based on the primer, uses cross-linked macromolecules, of which the unique structure require addition of no photoinitiator or just a small amount of photoinitiator for rapid UV curing, avoiding residual or votalization of a large number of small molecule photoinitiators in the coating, exhibiting excellent biological safety and compatibility. Meanwhile the coating process is simple and easy to control, which can create a uniform coating surface with appropriate thickness for medical catheters. The cross-linked macromolecules interact with water-soluble macromolecules to form a semi-interpenetrating network structure, leading to coating firmness. The water-swelling property of cross-linked macromolecules and water-soluble macromolecules provides the coating excellent lubricity and super hydrophilic. As a result, in the water environment of 0.1 MPa clamp force, the dynamic friction force is less than or equal to 0.12 Ibf, and the friction force is reduced by about 94% compared with the uncoated medical catheter.

The present invention adopts the above technical solution, and compared with the prior art, has the following technical effects:

(1) The solvents used are low-toxic alcohols such as ethanol, isopropanol or their mixture with water, which greatly solves problems caused other toxic organic volatile solvents (VOC) and minimizes the damage of organic solvents to workers.

(2) The primer coating uses polyester acrylic resin and the top coating uses cross-linked macromolecules. Compared with other water-based thermosetting coatings, the adhesion and UV curing speed are greatly improved, e.g. under the light intensity of 40-60 mw/cm$^2$, the cure could be done within 4 minutes, which is a great improvement for production efficiency.

(3) Due to the use of water-based or alcohol-soluble coating material as well as simple coating compositions, the preparation steps are greatly simplified, avoiding the cumbersome and time-consuming chemical reactions and the residual components caused by multi-step chemical reactions. The use of coating and the coating process are simple and easy to control, which can create a uniform coating surface with appropriate thickness.

(4) Due to the unique structure of cross-linked macromolecules, the rapid UV curing requires addition of no photoinitiator or just a small amount of photoinitiator, avoiding the disadvantages of residues and volatilization of a large number of small molecule photoinitiators in the coating, exhibiting excellent biosafety and biocompatibility.

(5) Cross-linked macromolecules interact with water-soluble macromolecules to form a semi-interpenetrating network structure, providing coating firmness, excellent lubricity and super hydrophilicity.

FIGURE

FIG. 1 is a curve chart of the frictional force test of the hydrophilic lubricating coatings for medical catheters in various embodiments of the present invention.

DETAILED DESCRIPTION

The present invention will be described in detail through following specific embodiments to deliver a better understanding of the present invention. However, the following embodiments do not limit the scope of the present invention.

Embodiment 1

Compositions of the primer coating: 2.0 g of 6-functional polyester acrylic resin, 0.4 g of hydroxyethyl methacrylate, 0.15 g of polyether-modified organosiloxane, 0.3 g of photoinitiator 2-hydroxy-2-methylphenylacetone, and 24 g of absolute ethanol are weighted and placed in a amber bottle, magnetically stirred for 2 hours, and filtered through a 500 mesh nylon gauze to obtain a mixed solution of the primer coating.

Compositions of the lubricating coating: 1.0 g of polyvinylpyrrolidone, 0.4 g of polyvinylpyridine, 0.2 g of polyethylene glycol, 0.1 g of polyoxyethylene, 12 g of water, and 31.3 g of absolute ethanol are weighed and placed in a amber bottle, magnetic stirred for 1-3 hours, and filtered through a 500 mesh nylon gauze to obtain a mixed solution of lubricating coating.

Embodiment 2

Compositions of the primer coating: 1.0 g of 3-functional polyester acrylic resin, 1.0 g of 6-functional polyester acrylic resin, 0.4 g of hydroxyethyl methacrylate, 0.15 g of polyether-modified organosiloxane, 0.3 g of photoinitiator 2-hydroxy-4'-(2-hydroxyethoxy)-2-methylbenzeneacetone (IRGACURE 2959), and 24 g of absolute ethanol are weighted and placed in a amber bottle, magnetically stirred for 2 hours, and filtered through a 500 mesh nylon gauze to obtain a mixed solution of the primer coating.

Compositions of the lubricating coating: 1.0 g of polyvinylpyrrolidone, 0.4 g of polyvinylpyridine, 0.2 g of polyethylene glycol, 12 g of water, and 31.3 g of absolute ethanol are weighed and placed in a amber bottle, magnetic stirred for 1-3 hours, and filtered through a 500 mesh nylon gauze to obtain a mixed solution of lubricating coating.

Embodiment 3

Compositions of the primer coating: 1.0 g of 3-functional polyester acrylic resin, 0.4 g of 6-functional polyester acrylic resin, 0.6 g of vinylpyrrolidone, 0.15 g of polyether-modified organosiloxane, 0.3 g of photoinitiator 2-hydroxy-4'-(2-hydroxyethoxy)-2-methylbenzeneacetone (IRGACURE 2959), and 24 g of absolute ethanol are weighted and placed in a amber bottle, magnetically stirred for 2 hours, and filtered through a 500 mesh nylon gauze to obtain a mixed solution of the primer coating.

Compositions of the lubricating coating: 1.0 g of polyvinylpyrrolidone, 0.4 g of polyvinylpyridine, 8.4 g of water, and 31.3 g of absolute ethanol are weighed and placed in a amber bottle, magnetic stirred for 1-3 hours, and filtered through a 500 mesh nylon gauze to obtain a mixed solution of lubricating coating.

Embodiment 4

Compositions of the primer coating: 5.0 g of 4-functional polyester acrylic resin, 1.8 g of hydroxyethyl methacrylate, 0.15 g of polyether-modified organosiloxane, 0.3 g of photoinitiator 2-hydroxy-2-methylphenylacetone (DAROCUR 1173), and 22.6 g of absolute ethanol are weighted and placed in a amber bottle, magnetically stirred for 2 hours, and filtered through a 500 mesh nylon gauze to obtain a mixed solution of the primer coating.

Compositions of the lubricating coating: 1.0 g of polyvinylpyrrolidone, 0.8 g of trimethylolpropane triacrylate, 2 g of water, 31.3 g of absolute ethanol, 0.2 g of polyethylene glycol, and 0.1 g of photoinitiator are weighed and placed in a amber bottle, magnetic stirred for 1-3 hours, and filtered through a 500 mesh nylon gauze to obtain a mixed solution of lubricating coating.

Embodiment 5

Compositions of the primer coating: 1.0 g of 3-functional polyester acrylic resin, 1.0 g of 6-functional polyester acrylic resin, 0.4 g of hydroxyethyl methacrylate, 0.15 g of polyether-modified organosiloxane, 0.3 g of photoinitiator 2-hydroxy-4'-(2-hydroxyethoxy)-2-methylbenzeneacetone (IRGACURE 2959), and 24 g of absolute ethanol are weighted and placed in a amber bottle, magnetically stirred for 2 hours, and filtered through a 500 mesh nylon gauze to obtain a mixed solution of the primer coating.

Compositions of the lubricating coating: 0.18 g of (15) ethoxylated trimethylolpropane triacrylate, 1.5 g of polyvinylpyrrolidone, 6 g of water, 31.3 g of absolute ethanol, and 0.06 g of photoinitiator 2-hydroxy-4'-(2-hydroxyethoxy)-2-methylphenylacetone (IRGACURE 2959) are weighed and placed in a amber bottle, magnetic stirred for 1-3 hours, and filtered through a 500 mesh nylon gauze to obtain a mixed solution of lubricating coating.

Embodiment 6

Compositions of the primer coating: 2.0 g of 4-functional polyester acrylic resin, 1.0 g of 6-functional polyester acrylic resin, 0.4 g of hydroxyethyl methacrylate, 0.15 g of polyether-modified organosiloxane, 0.3 g of 2-hydroxy-4 photoinitiator'-(2-Hydroxyethoxy)-2-methylbenzeneacetone (IRGACURE2959) as photoinitiator, and 24 g of absolute ethanol are weighted and placed in a amber bottle, magnetically stirred for 2 hours, and filtered through a 500 mesh nylon gauze to obtain a mixed solution of the primer coating.

Compositions of the lubricating coating: 1.0 g of polyvinylpyrrolidone, 0.8 g of waterborne polyurethane, 0.06 g of photoinitiator 2-hydroxy-4'-(2-hydroxyethoxy)-2-methylbenzeneacetone (IRGACURE 2959), 1.0 g of isopropanol, 8 g of water, and 31.3 g absolute ethanol are weighed and placed in a amber bottle, magnetic stirred for 1-3 hours, and filtered through a 500 mesh nylon gauze to obtain a mixed solution of lubricating coating.

The viscosity of the coatings in the above described embodiments were measured. It was found that the primer coating was about 1.3-2.0 mPa·s, and the lubricating coating was about 16-32 mPa·s.

Comparative Example 1

The commercially available jMed photocurable hydrophilic lubricating coating solution for medical catheters is used as a comparative example.

The medical catheter made of Pebax or Nylon material was wiped with a dust-free cloth and absolute ethanol and then coated with the Harland medical coating machine by dip coating. The sample catheter was immersed into the primer coating solution at a speed of 1.0-2.0 cm/s, soaked for 10 seconds, and taken out at a speed of 0.5-1.5 cm/s. It was then cured for 30 seconds to 2 minutes under the UV lamp. The sample catheter coated with the primer was immersed into the lubricating coating solution at a speed of 1.0-2.0 cm/s, soaked for 10 seconds and taken out at a speed of 0.5-1.5 cm/s. Finally, it was hung for 30 seconds to 90 seconds at rest, and cured for 240 s under the ultraviolet irradiation. The hydrophilic treatment of medical catheter was completed.

Coating Friction Test (1) PURPOSE

To study the lubricity and durability of the coating in the present invention.

(2) METHOD

The lubricated medical catheters were vertically fixed in the sink and soaked in water for 1 minute. A 0.1 Mpa pneumatic chuck with silicone venner surface was used to clamp and pull the catheters up vertically at a speed of 10 mm/s for a length of 10-15 cm. The curve chart of the frictional force against medical catheter coating surface was obtained.

(3) RESULTS

The test results was shown in Table 1 and FIG. 1.

TABLE 1

| Friction test cycles | Embodiment 1 | Embodiment 2 | Embodiment 3 | Embodiment 4 | Embodiment 5 | Embodiment 6 | Comparative example 1 |
|---|---|---|---|---|---|---|---|
| 1 | 0.085 | 0.066 | 0.071 | 0.091 | 0.115 | 0.085 | 0.097 |
| 2 | 0.083 | 0.063 | 0.071 | 0.092 | 0.116 | 0.075 | 0.107 |
| 3 | 0.081 | 0.060 | 0.069 | 0.088 | 0.116 | 0.07 | 0.099 |
| 4 | 0.083 | 0.065 | 0.072 | 0.088 | 0.112 | 0.068 | 0.101 |
| 5 | 0.082 | 0.067 | 0.072 | 0.091 | 0.113 | 0.07 | 0.102 |
| 6 | 0.085 | 0.062 | 0.071 | 0.099 | 0.106 | 0.069 | 0.099 |
| 7 | 0.082 | 0.063 | 0.072 | 0.087 | 0.113 | 0.072 | 0.100 |
| 8 | 0.080 | 0.065 | 0.073 | 0.089 | 0.118 | 0.072 | 0.098 |
| 9 | 0.081 | 0.062 | 0.069 | 0.095 | 0.115 | 0.075 | 0.107 |
| 10 | 0.083 | 0.063 | 0.070 | 0.091 | 0.113 | 0.069 | 0.106 |
| 11 | 0.082 | 0.062 | 0.069 | 0.096 | 0.118 | 0.068 | 0.109 |
| 12 | 0.082 | 0.063 | 0.070 | 0.088 | 0.115 | 0.071 | 0.105 |
| 13 | 0.082 | 0.061 | 0.071 | 0.091 | 0.115 | 0.073 | 0.106 |
| 14 | 0.083 | 0.060 | 0.072 | 0.101 | 0.114 | 0.08 | 0.111 |
| 15 | 0.081 | 0.066 | 0.071 | 0.088 | 0.116 | 0.068 | 0.114 |
| 16 | 0.082 | 0.065 | 0.070 | 0.089 | 0.115 | 0.081 | 0.112 |
| 17 | 0.081 | 0.064 | 0.069 | 0.090 | 0.113 | 0.082 | 0.105 |
| 18 | 0.083 | 0.065 | 0.068 | 0.091 | 0.115 | 0.081 | 0.111 |
| 19 | 0.085 | 0.063 | 0.068 | 0.087 | 0.113 | 0.082 | 0.110 |
| 20 | 0.082 | 0.065 | 0.068 | 0.090 | 0.115 | 0.083 | 0.107 |
| 21 | 0.083 | 0.062 | 0.068 | 0.092 | 0.116 | 0.079 | 0.106 |
| 22 | 0.086 | 0.063 | 0.069 | 0.091 | 0.118 | 0.078 | 0.105 |
| 23 | 0.082 | 0.062 | 0.068 | 0.093 | 0.118 | 0.082 | 0.103 |
| 24 | 0.081 | 0.065 | 0.069 | 0.095 | 0.117 | 0.083 | 0.107 |
| 25 | 0.081 | 0.066 | 0.069 | 0.096 | 0.117 | 0.081 | 0.109 |

The test results in Table 1 and FIG. 1 indicate that the light-cured hydrophilic coating solution of the present invention has a lower friction force, which is less than 0.12 lbf. The friction force of embodiment 5 is slightly higher than comparative example 1, while the embodiment 2 has the smallest friction force. The friction force of coatings of embodiment 1, 2, 3, 4 and 6 is about 0.06-0.1 lbf. And the friction force basically remains stable in 25 cycles tests. The friction force of embodiment 1, 2, 3, 4 and 6 is less than that of comparative example 1.

(4) CONCLUSION

The friction analysis of embodiments 1 to 6 and comparative example 1 reveals that the light-cured hydrophilic coating for medical catheter of the present invention has excellent lubricity and durability and its friction is reduced by about 94% compared with uncoated medical catheter (friction of the uncoated catheter is at least 1.8 lbf).

The detailedly described embodiments of the present invention are used as examples only. The present invention is not limited to the specific embodiments described above. For those skilled in the art, any equivalent modifications and substitutions to the present invention are also within the scope of the present invention. Therefore, equivalent transformations and modifications made without departing from the spirit and scope of the present invention should be covered within the scope of the present invention.

The invention claimed is:

1. A photocurable hydrophilic lubricating coating for a medical device, comprising a primer coating and a top coating, wherein the primer coating is attached to the device,
    wherein the primer coating includes: polyester acrylate 1-10 parts by weight of the primer coating, at least one solvent 50-90 parts by weight of the primer coating, a photoinitiator 0.5-5 parts by weight of the primer coating, at least one wetting agent 0.5-2 parts by weight of the primer coating and at least one active diluent 0.5-5 parts by weight of the primer coating,
    wherein the top coating consists of: one or more water-soluble macromolecules 1-10 parts by weight of the top coating, one or more cross-linked macromolecules 1-5 parts by weight of the top coating, at least one surfactant 0.1-1 part by weight of the top coating and a mixed solvent 50-98 parts by weight of the top coating,
    wherein said cross-linked macromolecules are oxygen-insensitive cross-linked substances, and has a light-absorbing functional group or a chromophore, and can self-luminously polymerize under UV light without adding a photoinitiator.

2. The photocurable hydrophilic lubricating coating for a medical device of claim 1, wherein said polyester acrylate is a water-soluble resin.

3. The photocurable hydrophilic lubricating coating for a medical device of claim 1, wherein said polyester acrylate is an aliphatic resin.

4. The photocurable hydrophilic lubricating coating for a medical device of claim 1, wherein said polyester acrylate has an unsaturated functionality with one or more oligomers selected from 3 functional polyester acrylate, 4 functional polyester acrylate and 6-functionality polyester acrylate.

5. The photocurable hydrophilic lubricating coating for a medical device of claim 1, wherein said solvent is selected from ethyl alcohol, propanol or isopropyl alcohol.

6. The photocurable hydrophilic lubricating coating for a medical device of claim 1, wherein photoinitiator of the said coating is one or more selected from 2-hydroxy-4'-(2-hydroxyethoxy)-2-methylpropiophenone, 2-hydroxy-2-methylpropiophenone, benzophenone and methyl benzoylformate.

7. The photocurable hydrophilic lubricating coating for a medical device of claim 1, wherein said wetting agent is selected from polyether modified organosilicone or polyether modified organosiloxane.

8. The photocurable hydrophilic lubricating coating for a medical device of claim 1, wherein said reactive diluent is one or more of single-functional active diluent and multi-functional active diluent.

9. The photocurable hydrophilic lubricating coating for a medical device of claim 8, wherein said reactive diluent is one or more of vinylpyrrolidone, hydroxyethyl methacrylate, ethoxyethoxyethyl acrylate and propylene oxide neopentyl glycol diacrylate.

10. The photocurable hydrophilic lubricating coating for a medical device of claim 1, wherein said water-soluble macromolecules are selected from one or more of polyvinylpyrrolidone, polyethylene glycol, polyethylene oxide, and polyvinyl alcohol.

11. The photocurable hydrophilic lubricating coating for the medical device of claim 1, wherein said one or more cross-linked macromolecules are water-soluble.

12. The photocurable hydrophilic lubricating coating for a medical device of claim 1, wherein said cross-linked macromolecules are capable of cross-linking to form a network structure, which is both water-insoluble and water-swellable.

13. The photocurable hydrophilic lubricating coating for a medical device of claim 1, wherein said cross-linked macromolecules are selected from one or more of polyvinyl alcohol pyridines, waterborne polyurethane, trimethylolpropane triacrylate.

14. The photocurable hydrophilic lubricating coating for a medical device of claim 1, wherein said surfactant is a water-soluble nonionic surfactant, and is selected from one or more of polyethylene glycol and polyethylene oxide.

15. The photocurable hydrophilic lubricating coating for a medical device of claim 1, wherein said mixed solvent is a mixture of alcohol and water, wherein the alcohol solvent is selected from ethanol, propanol or isopropanol.

16. A preparation method of a hydrophilic lubricating coating for medical catheters according to claim 1, it is characterized in the following steps:
    S1: Preparation of the primer coating:
        S11: Weigh each component by said parts of weight of the primer coating;
        S12: Add solvent, reactive diluent, photoinitiator and wetting agent into the polyester acrylate in sequence, and stir for 1-3 h in the dark to obtain the primer coating, which should be stored away from light;
    S2: Preparation of the top coating:
        S21: Weigh each component by said parts of weight of the top coating;
        S22: Add mixed solvent, cross-linked macromolecules and surfactant into the water-soluble macromolecules in sequence, and stir for 1-3 h in the dark to obtain the top coating, which should be stored away from light.

17. A method for using said photocurable hydrophilic lubricating coating according to claim 1, it is characterized in the following steps:
    S31: cleaning the medical device with ethanol and drying the medical device;

S32: applying said primer coating on the cleaned medical device by dipping, spraying or brushing, and curing the primer coating under ultraviolet light, S33: applying said top coating on the primer coating of the medical device by dipping, spraying or brushing, and curing the top coating under ultraviolet light.

* * * * *